(12) United States Patent
Gonzalez

(10) Patent No.: US 6,569,166 B2
(45) Date of Patent: May 27, 2003

(54) METHOD FOR EXPANDING THE THORAX

(75) Inventor: Hugo X. Gonzalez, Woodinville, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

(21) Appl. No.: 09/912,613

(22) Filed: Jul. 24, 2001

(65) Prior Publication Data

US 2001/0041906 A1 Nov. 15, 2001

Related U.S. Application Data

(62) Division of application No. 09/422,021, filed on Oct. 20, 1999, now Pat. No. 6,402,754.

(51) Int. Cl.[7] ............................................. A61B 17/64
(52) U.S. Cl. ......................................... 606/69; 606/74
(58) Field of Search ............................... 600/235, 219, 600/201; 606/69–71, 74, 105, 213, 215, 216, 191

(56) References Cited

U.S. PATENT DOCUMENTS

| | | | |
|---|---|---|---|
| 4,583,541 A | | 4/1986 | Barry |
| 4,852,552 A | * | 8/1989 | Chaux |
| 4,896,668 A | | 1/1990 | Popoff et al. |
| 5,356,412 A | | 10/1994 | Golds et al. |
| 5,415,658 A | | 5/1995 | Kilpela et al. |
| 5,772,583 A | * | 6/1998 | Wright et al. ............... 600/232 |
| 5,895,387 A | | 4/1999 | Guerrero et al. |
| 6,024,759 A | * | 2/2000 | Nuss et al. ................. 606/237 |
| 6,146,384 A | | 11/2000 | Lee et al. |

OTHER PUBLICATIONS

Isakov et al. "A New Method of Surgical Treatment of Funnel Chest with Help of Permanent Magnets", Chir. Pediatr., 1980, 21, pp. 361–362.*

Shamberger, "Congenital Chest Wall Deformities" Current Problems in Surgery vol. XXXIII, No. 6, Jun. 1996, pp. 470–543.*

April et al. "Correction of Funnel–Chest According to Senning–Johanson", Schweiz. Rundchau Med. (PRAXIS) 79, Nr. 12 (1980) pp 356–360.*

Ochsner et al. "Chone–Chondrosternon", Jounal of Thoracic Surgery, vol. 8, No. 5, Jun. 1939, pp. 469–511.*

* cited by examiner

Primary Examiner—Michael H. Thaler
(74) Attorney, Agent, or Firm—Graybeal Jackson Haley LLP

(57) ABSTRACT

A device and method treats pulmonary disease of a patient by expanding the thorax of the patient. Following surgical sternotomy, a separator is implanted in the thorax between the facing sternum surfaces resulting from the surgical sternotomy. The separator has a longitudinal dimension with opposing sidewalls extending along the longitudinal dimension and a width dimension. The facing surfaces of the sternum are engaged with the opposing sidewalls of the separator. Thereafter, the sternum is fixed to the separator for maintaining the sternum in engagement with the opposing sidewalls of the separator and thus maintaining the expanding condition of the thorax.

1 Claim, 5 Drawing Sheets

METHOD FOR EXPANDING THE THORAX

This is a divisional of prior application Ser. No. 09/422,021, filed Oct. 20, 1999, now U.S. Pat. No. 6,402,754 the benefit of the filing date of which is hereby claimed under 35 USC 120.

BACKGROUND OF THE INVENTION

The present invention is generally directed to an apparatus and method for treating Chronic Obstructive Pulmonary Disease (COPD). The present invention is more particularly directed to such an apparatus and method which may be implanted in the human body to expand the thorax and provide additional thoracic volume to support respiratory function.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and had increased 33% since 1979.

COPD affects the patient's whole life. It has three main symptoms: cough; breathlessness; and wheeze. At first, breathlessness may be noticed when running for a bus, digging in the garden, or walking up hill. Later, it may be noticed when simply walking in the kitchen. Overtime, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled B-agonists. For those patients who respond poorly to the foregoing or who have persistent symptoms, Ipratropium bromide may be indicated. Further, courses of steroids, such as corticosterocds, may be required. Lastly, antibiotics may be required to prevent infections and influenza and pneumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopped remitting for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

LVRS is a long and tedious procedure, fraught with potential complications. Infection is always a concern. Further, lung tissue is difficult to suture and seal making leakage a serious potential problem.

Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

While, lung transplantation is also an option, lung transplantation is considered for only those with advanced COPD. Given the limited availability of donor organs, lung transplants are far from being available to all patients.

In view of the foregoing, there is a need in the art for a new and improved therapy for COPD. More specifically, there is a need for such a therapy which could be made available to all COPD patients and which provides more permanent results than pharmacotherapy while being less traumatic than LVRS. The present invention is directed to an apparatus and method which provide such an improved therapy for COPD.

SUMMARY OF THE INVENTION

The present invention provides a device and method for treating chronic obstructive pulmonary disease by expanding the thorax of a patient to an expanded condition and maintaining the thorax in the expanded condition. In accordance with one aspect of the present invention, a separator is implanted within the thorax. The separator expands the thorax to the expanded condition. At least one fastener, for example stainless steel suture wire, maintains the separator within the thorax and thereby maintains the expanded condition of the thorax.

In accordance with further aspects of the present invention, the thorax expansion is implemented by an implantable assembly which includes a separator having opposed sidewalls for engaging facing sidewalls of a sternum resulting from surgical sternotomy. The separator has a longitudinal dimension with the opposed sidewalls extending along the longitudinal dimension, and a width dimension, transverse to the longitudinal dimension, separating the opposed sidewalls of the separator and the facing sidewalls of the sternum. As a result, the volume of the thorax is increased and maintained in an expanded condition.

In accordance with further aspects of the present invention, the separator includes a base having a surface extending from each opposed sidewall. The surface extending from each opposed sidewall supports the sternum when the facing sidewalls of the sternum are engaged with the opposed sidewalls of the separator. Preferably, the opposed sidewalls of the separator have a transverse dimension approximately equal to the thickness of the sternum at the facing sidewalls.

The separator is formed of a biocompatible material such as stainless steel or titanium. Alternatively, the separator may be formed of a biocompatible material and include a ceramic covering.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings in the several figures of which like reference numerals identify identical elements, and wherein:

DETAILED DESCRIPTION

Figure 1:
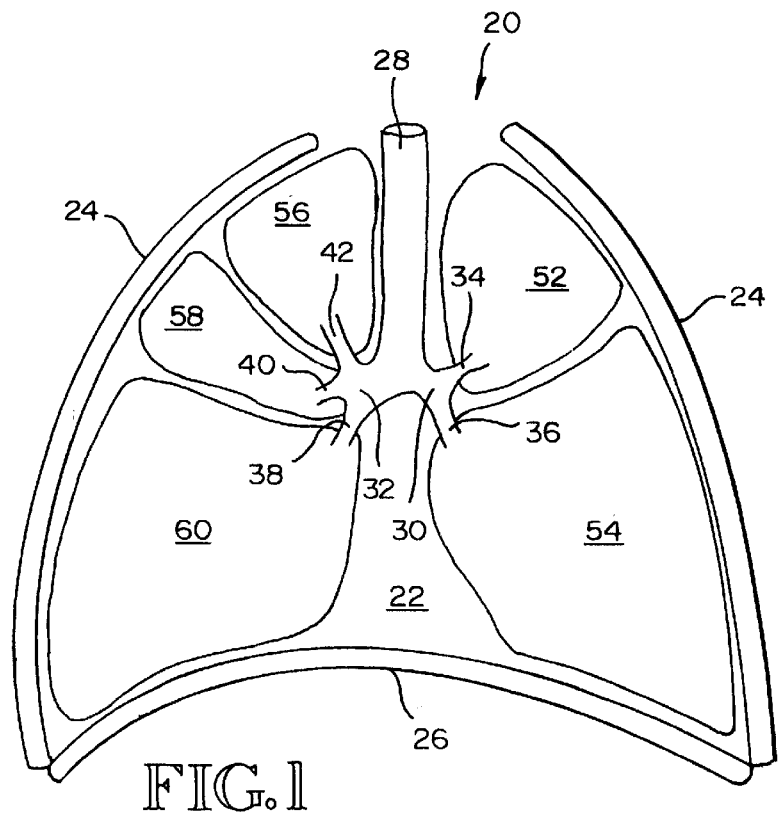
FIG. 1 is a simplified sectional view of a thorax illustrating a healthy respiratory system.

Referring now to FIG. 1, it is a sectional view of a healthy respiratory system 20. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, and the bronchial branches 34, 36, 38, 40, and 42. The respiratory system 20 further includes left lung lobes 52 and 54 and right lung lobes 56, 58, and 60. Each bronchial branch communicates with a respective different portion of a lung lobe, either the entire lung lobe or a portion thereof.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
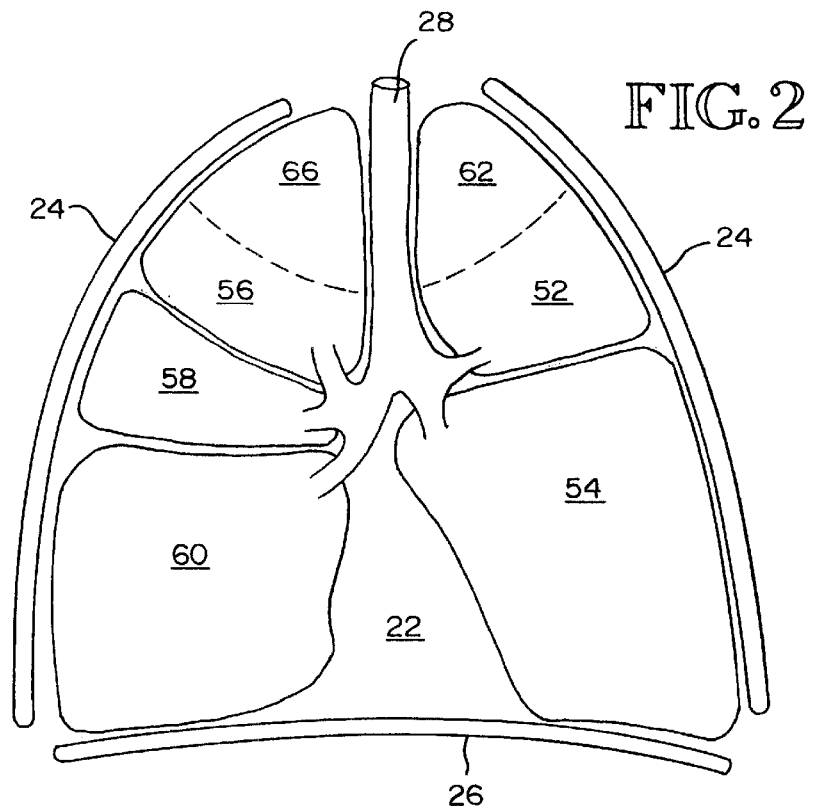
FIG. 2 is a sectional view similar to FIG. 1 but illustrating a respiratory system suffering from COPD.

In contrast to the healthy respiratory system of FIG. 1, FIG. 2 illustrates a respiratory system suffering from COPD.

Here it may be seen that the lung lobes 52, 54, 56, 58, and 60 are enlarged and that the diaphragm 26 is not arched but substantially straight. Hence, this individual is incapable of breathing normally by moving the diaphragm 26. Instead, in order to create the negative pressure in the thorax 22 required for breathing, this individual must move the chest wall outwardly to increase the volume of the thorax. This results in inefficient breathing causing these individuals to breathe rapidly with shallow breaths. The apex portion 62 and 66 of the upper lung lobes 52 and 56, respectively, are most affected by COPD.

The apparatus and method of the present invention treats COPD by deriving the benefits of lung volume reduction surgery without the need of performing lung volume reduction surgery. As will be seen hereinafter, the present invention contemplates permanent expansion of the thorax 22. This leaves extra volume within the thorax for the diaphragm to assume its arched state for acting upon the healthy lung tissue. As previously mentioned, this should result in improved pulmonary function due to enhanced elastic recoil, correction of ventilation/perfusion mismatch, improved efficiency of respiratory musculature, and improved right ventricle filling.

Figure 3:
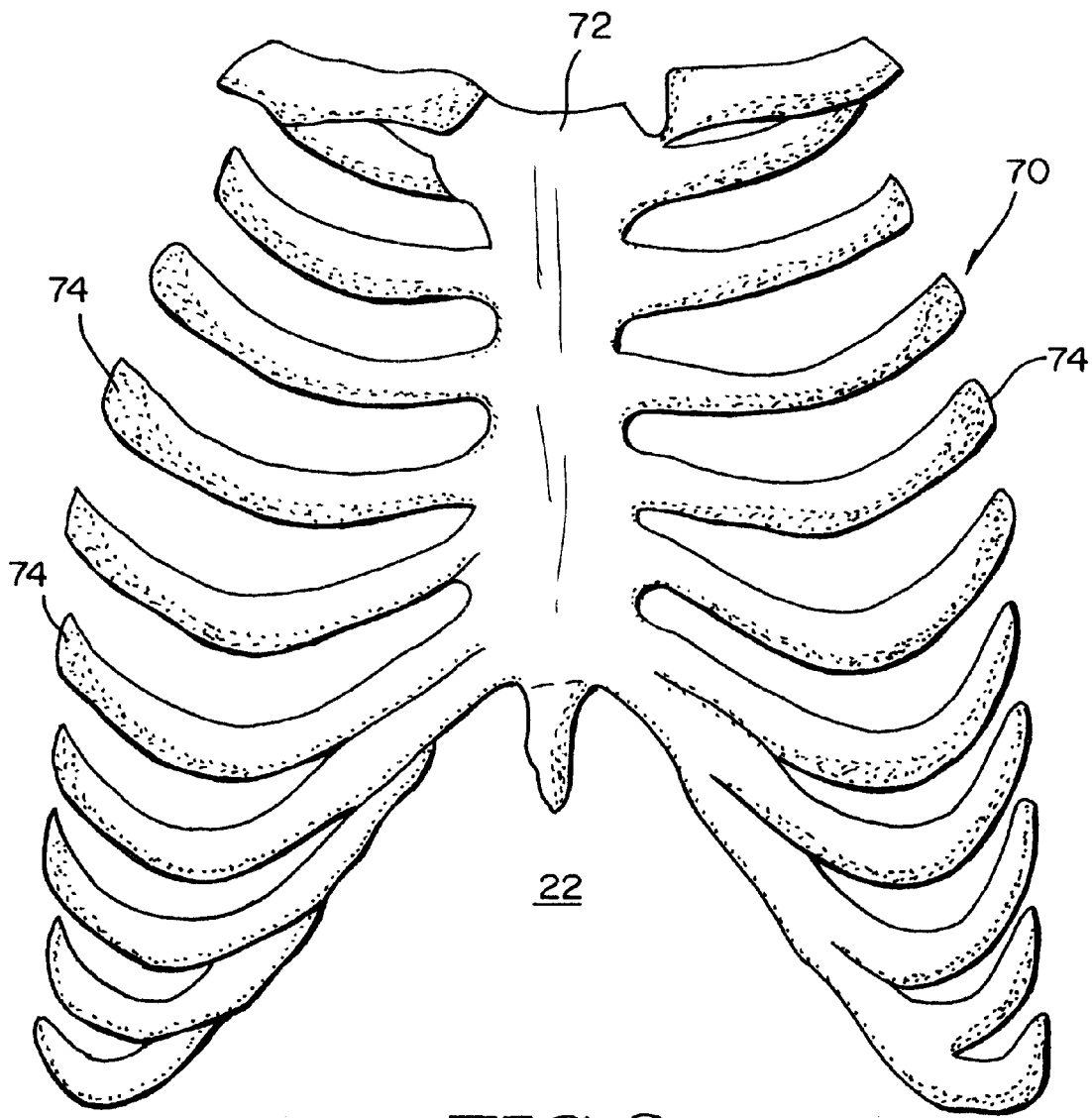
FIG. 3 is a front view of a human rib cage which defines the human thorax.

Referring now to FIG. 3, it illustrates a rib cage 70 of a human. The rib cage 70 forms the chest wall 24 (FIG. 1) defining the thorax 22. The rib cage includes the sternum 72 which is a plate of bone forming the middle of the anterior wall of the thorax. Extending arcuately from the sternum 72 are the ribs 74.

The volume that the thorax occupies may be approximated to that of a cylinder. Since the volume of a cylinder is proportional to the square of the cylinder circumference, a 12% increase in a cylinder circumference provides about a 30% increase in the cylinder volume. Hence, approximately a 12% increase in a patient's chest measurement would yield about a 30% increase in thoracic volume.

In accordance with a preferred embodiment of the present invention, a sternotomy is performed on the sternum 72. This is a common surgical procedure wherein the sternum is opened in the midline during open chest surgery and is thus well known. It results in exposed facing sternum surfaces. Further, in accordance with the preferred embodiment, the exposed facing sternum surfaces are separated and a filler or separator is disposed inbetween. The sternum is then sutured with suture wire to the separator for maintaining the thorax in an expanded condition. The amount of thorax expansion is of course dependent upon the condition and anatomy of each patient. However, as an example, a 5 to 15% increase in thorax diameter would be sufficient to obtain the benefits otherwise achieved with LVRS.

Figure 4:
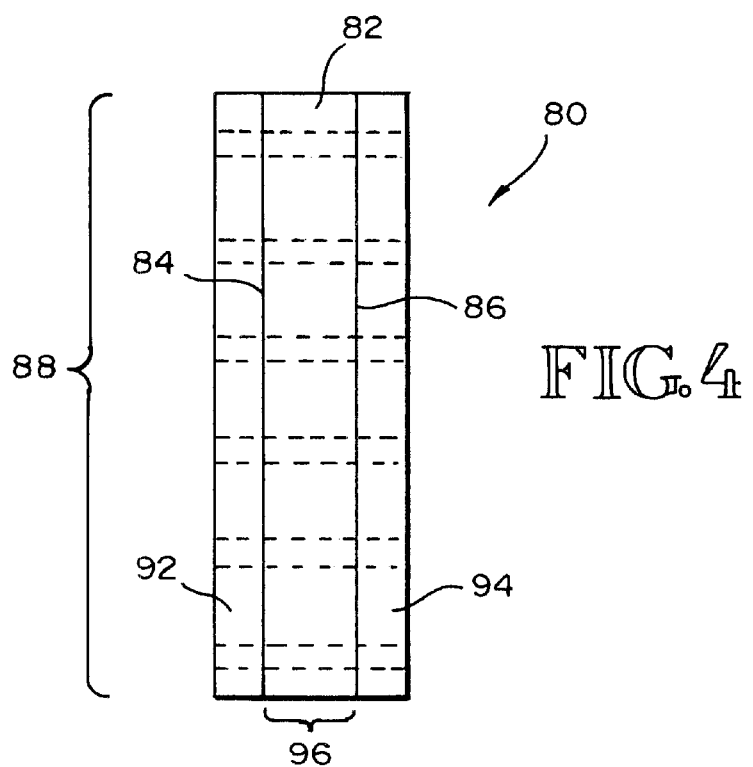
FIG. 4 is a top plan view of the thorax expander embodying the present invention.
Figure 5:
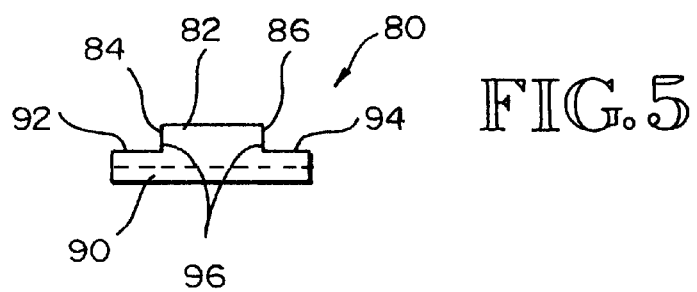
FIG. 5 is an end plan view of the thorax expander of FIG. 4.
Figure 6:
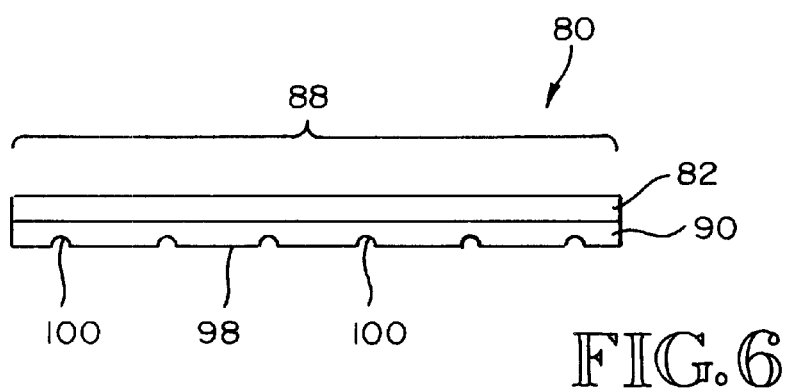
FIG. 6 is a side plan view of the thorax expander of FIG. 4.

Referring now to FIGS. 4, 5, and 6, they provide top, end, and side plan views respectively of a thorax expanding device 80 embodying the present invention. The device includes a separator 82 having opposed sidewalls 84 and 86 along its longitudinal dimension 88. The device 80 further includes a base 90 having surfaces 92 and 94 extending from opposed sidewalls 84 and 86 respectively. As will be seen hereinafter, the opposed sidewalls 84 and 86 have a transverse dimension approximately equal to the thickness of the sternum at its midline. The separator also includes a width dimension 96, transverse to the longitudinal dimension 88, which defines the separation of the sidewalls 84 and 86 and the extent of increase in the thorax circumference.

As will be seen hereinafter, the device 80 may be sutured to the sternum with, for example, suture wire, to maintain the sternum in engagement with the device 80 and to thus maintain the expansion of the thorax. To that end, it will be seen in FIG. 6 that the bottom surface 98 of the base 90 includes a plurality of grooves 100 which are arranged to maintain the suture wires in fixed and spaced apart relation.

Figure 7:
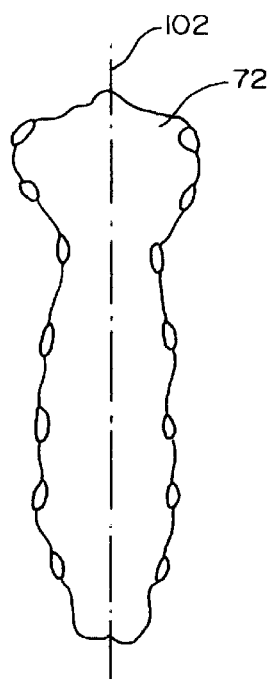
FIG. 7 is a front plan view of a human sternum.
Figure 8:
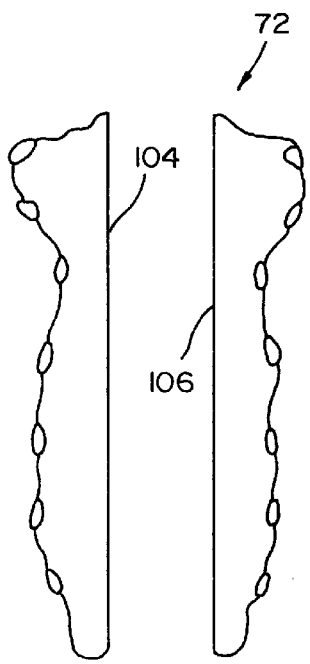
FIG. 8 is a front plan view of the human sternum of FIG. 7 after a surgical sternotomy.

Referring now to FIG. 7 it illustrates a front plan view of the sternum 72. As will be seen in FIG. 7, the sternum 72 has a midline 102. During a surgical sternotomy, the physician cuts the sternum 72 along the midline 102. As will be seen in FIG. 8, this results in the sternum 72 having exposed facing surfaces 104 and 106. In accordance with the present invention, following the surgical sternotomy, the facing exposed surfaces 104 and 106 of the sternum 72 are separated. Thereafter, the device 80 is implanted in the thorax as may be seen in FIGS. 9 and 10.

Figure 9:
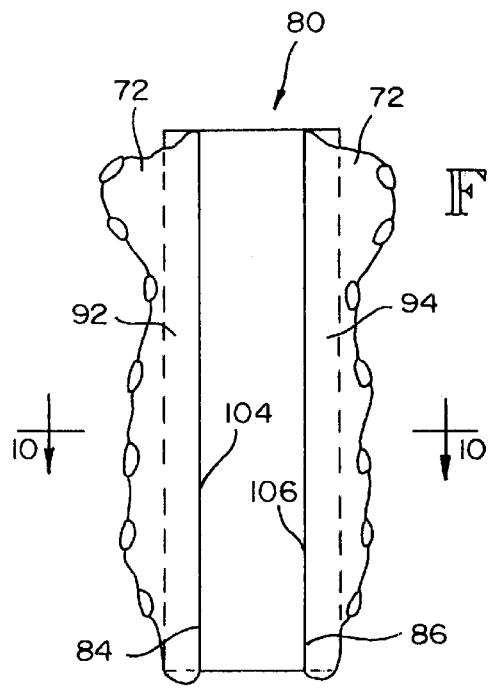
FIG. 9 is a front plan view of the sternum of FIG. 8 in engagement with a thorax expander embodying the present invention.
Figure 10:
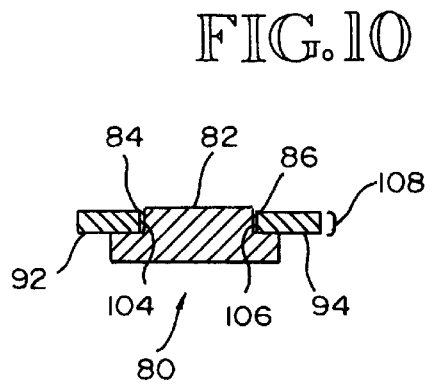
FIG. 10 is a cross-sectional view taken along lines 10—10 of FIG. 9.

In FIGS. 9 and 10, the exposed facing surfaces 104 and 106 of the sternum are brought into engagement with the opposing sidewalls 84 and 86 respectively of the separator 82. Also, the bottom of the sternum is supported by the surfaces 92 and 94 of the base. It may also be noted in FIG. 10 that the transverse dimension of the sidewalls 84 and 86 is approximately equal to the thickness 108 of the sternum at the exposed facing surfaces 104 and 106.

Figure 11:
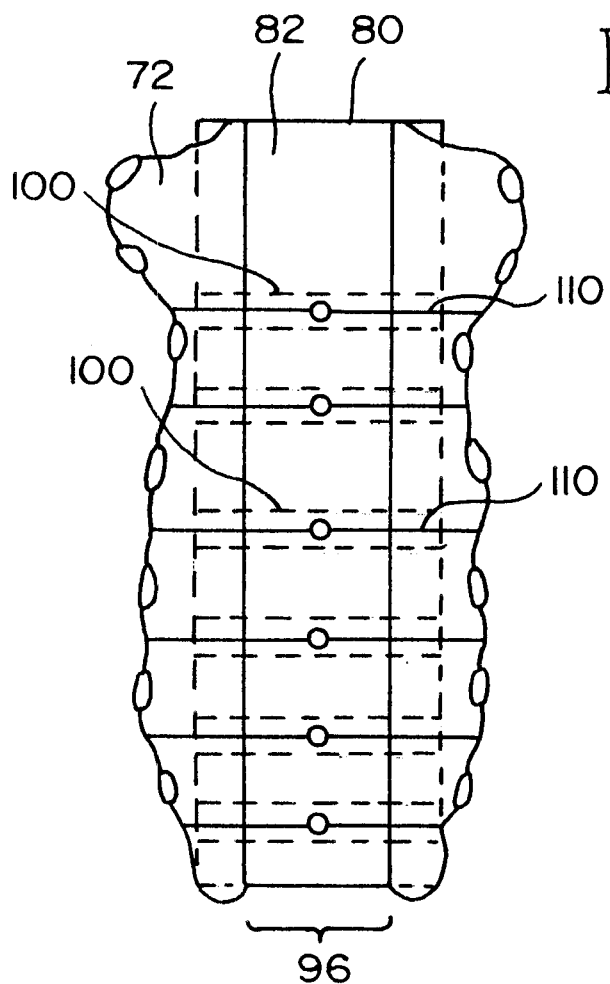
FIG. 11 is a front plan view of the sternum of FIG. 7 in maintained engagement with the thorax expander embodying the present invention for maintaining the thorax in an expanded condition.

Once the device 80 is positioned inbetween the sternum halves resulting from the surgical sternotomy, the sternum 72 is fixed to the device 80. In accordance with this embodiment, as may be seen in FIG. 11, the sternum is fastened to the device 80 with suture wires which are disposed in the channels in the bottom of the base 90. The suture wires 110 and are preferably formed of stainless steel as is well known in the art. Other fasteners which may be used in place of the suture wires 110 and are well known in the art.

Once the suture wires 110 are fixedly holding the sternum to the device 80, the procedure is complete. As a result, the volume of the thorax will be expanded because the circumference of the thorax will be increased by the width dimension 96 of the separator 82.

Figure 12:
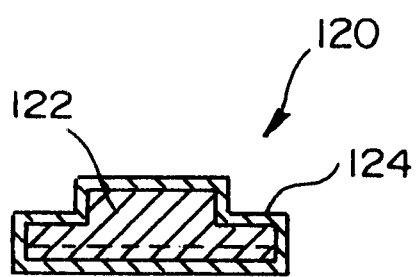
FIG. 12 is a cross-sectional side view of another thorax expander embodying the present invention.

The device 80 is preferably formed of a biocompatible material. Materials suitable for the device 80 may be, for example, stainless steel or titanium. In addition, as illustrated in FIG. 12, a device 120 is shown configured similar to the device 80 of FIGS. 4 through 6 but in addition, it has a body of biocompatible material of, for example, stainless steel or titanium or a ceramic coating 124. In all other respects, the device 120 is essentially identical to the device 80 and may be utilized in the same manner.

As can thus be seen from the foregoing, the present invention provides an apparatus and method for treating COPD by expanding the thorax. The thorax expansion is achieved through the permanent implantation of a separator which separates the sternum following surgical sternotomy. The foregoing is achieved without the need for removing lung tissue. Following the treatment, the thorax will have an increased volume providing room for the diaphragm to assume its arcuate state to assist in normal breathing and to achieve the benefits of lung volume reduction.

While particular embodiments of the present invention have been shown and described, modifications may be made. It is therefore intended in the appended claims to cover all such changes and modifications which fall which fall within the true spirit and scope of the invention.

What is claimed is:

1. A method of expanding a thorax and maintaining the thorax in an expanded condition, the method including the steps of:

performing a surgical sternotomy on the sternum of the thorax to form exposed facing sternum surfaces along the midline of the sternum;

separating the sternum sidewalls;

providing a separator having a longitudinal dimension, opposing sidewalls extending along the longitudinal dimension, and a width dimension transverse to the longitudinal dimension;

positioning the separator between the exposed sternum surfaces:

engaging the exposed surfaces of the sternum with the opposing sidewalls of the separator; and permanently fixing the sternum to the separator for maintaining the facing surfaces of the sternum in engagement with the opposing sidewalls of the separator, wherein the separator includes a base extending from the opposing sidewalls and wherein the positioning step includes resting the sternum on the base when engaging the exposed facing sternum surfaces with the separator opposing sidewalls.

* * * * *